United States Patent [19]
Elias et al.

[11] Patent Number: 5,643,899
[45] Date of Patent: Jul. 1, 1997

[54] LIPIDS FOR EPIDERMAL MOISTURIZATION AND REPAIR OF BARRIER FUNCTION

[75] Inventors: Peter M. Elias, Muir Beach; Kenneth R. Feingold, San Rafael, both of Calif.; Carl R. Thornfeldt, Ontario, Oreg.

[73] Assignees: Cellegy Pharmaceuticals, Inc., Foster City; The Regents of the University of California, Oakland, both of Calif.

[21] Appl. No.: 347,363

[22] PCT Filed: Jun. 18, 1993

[86] PCT No.: PCT/US93/05798

§ 371 Date: Feb. 27, 1995

§ 102(e) Date: Feb. 27, 1995

[87] PCT Pub. No.: WO94/00127

PCT Pub. Date: Jan. 6, 1994

Related U.S. Application Data

[63] Continuation-in-part of Ser. No. 952,934, Sep. 29, 1992, abandoned, and Ser. No. 953,603, Sep. 29, 1992, abandoned, which is a continuation-in-part of Ser. No. 901,052, Jun. 19, 1992, abandoned.

[51] Int. Cl.$^6$ .......................... A61K 31/59; A61K 31/23; A61K 31/20; A61K 31/16
[52] U.S. Cl. .......................... 514/171; 514/182; 514/552; 514/558; 514/625; 514/847
[58] Field of Search .......................... 514/847

[56] References Cited

FOREIGN PATENT DOCUMENTS

| | | |
|---|---|---|
| 0097059 | 7/1985 | European Pat. Off. . |
| 0278505 | 2/1988 | European Pat. Off. . |
| 61-260008 | 11/1986 | Japan . |
| 62-192703 | 2/1987 | Japan . |
| 2013792 | 2/1988 | Spain . |
| 2178312 | 6/1986 | United Kingdom . |
| WO86/00015 | 1/1986 | WIPO . |
| WO90/01323 | 8/1989 | WIPO . |

OTHER PUBLICATIONS

Wertz, P.W., et al., Essential Fatty Acids and Epidermal Integrity., Arch. Detmatol. vol. 123, pp. 1381–1384, (1987).
William Abraham, et al., "Effect of Epidermal Acylglucosylceramides and Acylceramides on the Morphology of Liposomes Prepared From Statum Corneum Lipdis, Biochimica et Biophysica Acta 939", 403–408, (1988) Elsevier.
Imokawa, G., et al., "Importance of Intercellular Lipids in Water–retention Properties of the Stratum Corneum: Induction and Recovery Study of Surfactant Dry Skin", Arch. Dermatol Res., 281:45–51, (1989).
Hawley's Condensed Chemical Dictionary, Eleventh Edition Revised by Van Nostrand Reinhold, p. 507, (1987).
Schurer et al., "The Biochemistry and Function of Stratum Corneum Lipids", Advances in Lipid Research, vol. 24, by Academic Press, Inc., pp. 27–56, (1991).

Elias et al., "Structural and Lipid Biochemical Correlates of the Epidermal Permeability Barrier, Advances in Lipid Reserch", vol. 24, by Academic Press, Inc., pp. 1–26, (1991).
Abraham et al., "Fusion Patterns of liposomes Formed from Stratum Corneum Lipids, The Society for Investigative Dermatology, Inc.," pp. 259–262, (1988).
Imokawa, G., et al., "Selective Recovery of Deranged Water–Holding Properties by Stratum Corneum Lipids", The Journal of Investigation Dermatology, vol. 87, No. 6., pp. 758–761, (1986).
Wertz, P.W. et al., "Covalently Bound Lipids of Human Stratum Corneum", The Journal of Investigative Dermatology, vol. 92, No. 1, pp. 109–111, (1989).
Cullis, P.R., et al., "The Bilayer Stabilizing Role of Sphingomyelin in the Presence of Cholesterol", Biochemical et Biophysica Acta, vol. 597, pp. 533–542, (1980).
Proksch, E., et al., "Barrier Function Regulates Epidermal DNA Synthesis", The Journal of Clinical Investigation, vol. 87, pp. 1668–1673, (1991).
Wertz, P.W., et al., "Hydroxyacid Derivatives in Human Epidermis", Lipdis, vol. 23, No. 5 (1988).
Ansari, M.N.A., et al. "Fatty Acid Composition of the Living Layer and Stratum Corneum Lipids of Human Sole Skin Epidermis", Lipids, vol. 5, No. 10, pp. 838–845 (1970).
Monash, S. et al., "Location and Re–Formation of the Epithelial Barrier to Water Vapor", A.M.A. Arch. of Dermatology, vol. 78, pp. 710–714, (1958).
Yardley, H.J., et al., "Lipid Composition and Metabolism in Normal nd Diseased Epidermis", Pharmac. Ther. vol. 13, pp. 357–383, (1981).
Abraham, W., et al., "Interaction Between Corneocytes and Stratum Corneum Lipid Liposomes in vitro", Biochemica et Biophysica Acta, vol. 1021, pp. 119–125, (1990).
Man et al., "Exogenous Lipids Influence Permeability Barrier Recovery in Acetone–Treated Murine Skin", Arch. Dermatol–vol. 129, pp. 728–738, (1993).
Review Article, European Journal of Dermatology, 1: 39–43, (1991) "Skin Ceramides: Structure and Function".
Imokawa, G., et al., "Stratum Corneum Lipids Serve as a Bound–Water Modular", The Society for Investigative Dermatology, Inc., pp. 845–850 (1991).

*Primary Examiner*—Shelley A. Dodson
*Attorney, Agent, or Firm*—Townsend and Townsend and Crew LLP

[57] ABSTRACT

Disorders of the skin and mucous membrane that have a disrupted or dysfunctional epidermal barrier are treated or prevented by topical application of a formulation comprising certain of the three major epidermal lipid species or their structurally similar precursors, isomers, or analogs in certain proportion ranges. This invention utilizes the following lipid species in unique combinations of two or more components: cholesterol, an acylceramide, a ceramide, and essential and nonessential fatty acids. These combinations are effective both as moisturizing agents and agents for the restoration of barrier function. Some of these combinations are further enhanced by the addition of known moisturizers such as petrolatum and glycerine.

20 Claims, No Drawings

LIPIDS FOR EPIDERMAL MOISTURIZATION AND REPAIR OF BARRIER FUNCTION

CROSS REFERENCE TO RELATED APPLICATIONS

This application is a continuation-in-part of applications Ser. No. 07/952,934 and Ser. No. 07/953,603 both filed on Sep. 29, 1992, Ser. No. 07/953,603 being a continuation-in-part of Ser. No. 07/901,052, filed Jun. 19, 1992, all of which are now abandoned.

This invention was made with Government support under Grant No. AR-19098, awarded by the National Institutes of Health. The Government has certain rights in this invention.

This invention resides in the area of topical formulations for application to skin. Among the various effects sought by the administration of such formulations are emolliation and hydration, as well as repair of the epidermal barrier function. In particular, this invention relates to the application of lipids and lipid formulations and to the treatment of subjects suffering from skin or mucous membrane diseases or disorders which display epidermal hyperproliferation and disruptions of the barrier function.

BACKGROUND OF THE INVENTION

The skin is the largest organ of the body and protects mammalian organisms from both aqueous and xerotic ambient environments. The maintenance of a barrier against excessive transcutaneous water loss to the environment is critical to survival of all terrestrial animals. In mammals, this barrier is formed by the anucleate, cornified, outermost layers of the epidermis, collectively known as the stratum corneum. Both the surfaces of mucous membranes and the deepest layers of the stratum corneum contain high concentrations of glycosphingolipids which are metabolized progressively to ceramides as the stratum granulosum becomes anucleate with outward maturation. Localized or generalized perturbations of the epidermal barrier occur in a variety of diseases and conditions of the skin and mucous membrane. These perturbations not only contribute significantly to the morphology of the cutaneous lesions, but also activate certain skin diseases, for example the Koebner phenomenon in psoriasis. Common moisturizers and emollients also cause disruptions of the barrier function.

It is now generally accepted that the intercellular, lamellar bilayer sheets of stratum corneum lipids are the key constituents for a functional barrier. The epidermal lipids consist of a mixture of polar and nonpolar species. The three dominant lipids by weight are ceramides (40%), cholesterol (20–25%) and free fatty acids (20–25%). The latter group include the essential fatty acid, linoleic acid, as well as additional nonessential fatty acids. The human epidermis further contains a unique acylsphingolipid whose molecular structure includes a sphingoid backbone with a 30-carbon, α-hydroxy acid residue joined to the backbone through an amide linkage, the residue itself being ω-esterified with linoleic acid.

Although each of the lipid species is important for stratum corneum homeostasis, ceramides are of particular importance because of their large weight contribution and structural characteristics. The moisturization properties of ceramides are known. A published Japanese patent application of Kao Company Limited (No. 24391-1987) discloses a formulation containing bovine ceramide with a sphingoid base of 10 to 26 carbon atom length and one or more of any of the other stratum corneum lipids. The purpose of this formulation is to increase water retention and improve skin roughness (moisturization).

Despite the potential efficacy of lipids as moisturizer ingredients, studies have demonstrated that many of the individual lipids, including ceramides and lipid combinations which are disclosed in the Kao disclosure for their moisturization properties, actually impede rather than facilitate barrier repair when applied to damaged skin. Formulations of this kind will therefore worsen the lesions of skin and mucous membrane diseases because an acute or chronically damaged epidermal barrier responds differently than either normal skin or merely dry, rough skin when epidermal lipids are applied.

While substances which effect barrier repair are all effective as moisturizers as well, the converse is not true. For example, scaling and roughness of the skin are a manifestation of an abnormally desquamating stratum corneum, but often these conditions do not correlate with the function of the stratum corneum barrier. Patients suffering from atopic dermatitis, for example, have skin with an incompetent barrier, as measured by trans-epidermal water loss, but no visible scaling.

Moisturizers are defined as substances which increase the stratum corneum water content. Skin conductance measurements are the most accurate assay of the water content. High skin conductance measurements indicate high water content. While high water content indicates a high degree of moisturization, it is not an indication of good barrier function. Mucous membranes, for example, are moist with an extremely high water content but poor barrier function. Nor does the thickness of the stratum corneum correlate with barrier function. Palms and soles which appear normal have the thickest stratum corneum and a high water content but relatively poor barrier function.

While all moisturizers will temporarily decrease visible scaling and roughness, they usually offer little or no improvement to the integrity of the stratum corneum barrier.

The importance of the three major epidermal lipids to the integrity of the epidermal barrier is demonstrated by their increased synthesis after both acute and chronic barrier disruption. Inhibition of their respective rate-limiting enzymes causes a reduction in concentration of any one of these three major epidermal lipids and thereby produces significant delay in the recovery of barrier function.

Lovastatin, an inhibitor of cholesterol synthesis, produces a barrier defect when applied to normal epidermis. After lovastatin is applied, cholesterol synthesis rapidly normalizes, but fatty acid synthesis remains elevated. This suggests that a disturbance in the fatty acid:cholesterol ratio accounts for the perturbed barrier function.

Although logic would suggest that application of each of the lipids individually or with another lipid in a two-component system should accelerate barrier recovery when applied to damaged skin, this does not in fact occur. For example, in mice which suffer a barrier defect due to a deficiency in the essential fatty acid, linoleic acid, topical application of linoleic acid alone further aggravates barrier dysfunction until the systemic deficiency state is corrected.

The following are situations and cutaneous conditions which involve or give rise to a disrupted or dysfunctional epidermal barrier:

1) Important causes of morbidity and mortality in premature infants less than 33 weeks of gestational age are fluid and electrolyte abnormalities, hypothermia, and infection with the skin being the portal of entry. The development of mature barrier function coincides with the deposition of adequate amounts of the three major epidermal lipids in appropriate proportions.

2) Eczematous dermatitides are a group of inflammatory hyperproliferative skin diseases characterized by poorly demarcated, scaly, itchy or tender patches that may involve wide-spread areas of the body. Two of the most common types are atopic and seborrheic dermatitis. Both have a genetic predisposition and display abnormalities of stratum corneum lipids and barrier function even in clinically uninvolved skin. The other major eczematous dermatitides result from environmental or occupational insults of solvents, chemicals, detergents, hot water, low ambient humidity, ultraviolet or X radiation. These disorders include allergic or irritant contact dermatitis, eczema craquelée, photoallergic, phototoxic, or phytophotodermatitis, radiation, and stasis dermatitis. Eczema craquelée begins as dehydrated or dry skin that reaches such severity that complete destruction of the epidermal barrier occurs, which results in inflammation and hyperproliferation. The predominant therapy for eczematous dermatitides comprises topical corticosteroids and systemic antihistamines with or without antibiotics. Unfortunately, the skin remains excessively sensitive for months after the apparent clinical resolution of the lesions which results in rapid rebound of the lesions with significantly less environmental insult. Therefore, there is a great need for an effective therapeutic formulation that will normalize the barrier of both clinically uninvolved and involved skin to prevent disease exacerbations and/or limit disease extent.

3) Ulcers and erosions result from trauma or ischemia of the skin or mucous membranes. These insults include chemical or thermal burns, and vascular compromise as in venous, arterial, embolic or diabetic ulcers. The lesions are not only painful but form a portal for pathogenic microbes. Current therapy consists primarily of antibiotics, occlusive dressings, and vascular compression bandages.

4) The ichthyoses are a group of incurable, disfiguring common to rare genetic diseases characterized by disorders of abnormal epidermal cornification with or without associated abnormal barrier function and epidermal hyperproliferation. The palliative treatments for these diseases consist of systemic and topical retinoids, and topical α-hydroxy and salicylic acids. These modalities can produce significant topical irritation and both systemic retinoids and topical salicylic acid carry a significant risk of serious systemic toxicity.

5) The epidermolysis bullosae are a group of rare genetic diseases resulting from an absence or defect in epidermal/dermal cohesion. Cutaneous trauma to normal skin with normal daily activity results in complete or partial loss of the epidermis producing blisters, erosions, and ulcers. The only therapy for one type is diphenylhydantoin and/or systemic retinoids. Both treatments produce a significant number of severe systemic side effects with chronic usage.

6) Psoriasis is a markedly hyperproliferative, inflammatory papulosquamous disease characterized by sharply demarcated, scaly plaques most frequently located at areas of the body which suffer trauma, specifically knees, elbows, hands, feet, and scalp. Nearly all of the currently available topical and systemic therapies carry a significant risk of systemic and/or cutaneous toxicity. Moreover, these treatments generally are followed by a rapid rebound of the disease when they are withdrawn. None of these treatments repair the barrier and some actually worsen it. The current medications include: retinoids, corticosteroids, sulfones, antineoplastic agents, anthralin, tar, psoralens and ultraviolet A or B light. It has recently been reported that prolonged remission was achieved in 60% of lesions treated with weekly applications of occlusive tape for a 10-week period. This modality artificially restores epidermal barrier function to some degree.

7) The cutaneous changes of intrinsic aging and photoaging (dermatoheliosis) result from environmental ravages combined with intrinsic changes which produce atrophy, fragility, inelasticity, decreased cell cohesion, hypoproliferation, and delayed healing after insults to the barrier. The stratum corneum lipids display a depletion of ceramide and nonpolar lipid species with a relative increase in cholesterol. The current treatments consist of topical application of retinoids or α-hydroxy acids, both of which often produce irritation, especially in the elderly.

8) The limiting factor for occupational or athletic performance, even for the occasional recreational athlete is frictional blistering of the skin by mechanical shearing forces. Prevention with layered clothing or application of synthetic films are the only currently available, somewhat helpful remedies.

9) The major limiting factor for the topical use of corticosteroids, especially in the young and elderly is cutaneous atrophy which predisposes to infection and slows the rate of healing. Topical retinoids and α-hydroxy acids may partially reverse the atrophy, but the irritation potential of these agents is significantly increased.

10) There are many known or potential therapeutic compounds whose utility has been prevented or is compromised because of cutaneous irritation or barrier disruption. A formulation comprising these compounds incorporated with the lipids of this invention will expand the therapeutic armamentarium potentially available to physicians.

The integrity of the epidermal barrier is known to be the major factor that regulates epidermal DNA synthesis. It is also known that maintenance of a normal epidermal barrier will inhibit epidermal hyperproliferation. The discoveries of the present invention, therefore, lead to treatments for hyperproliferative cutaneous diseases, notable examples of which are papulosquamous and eczematous diseases.

SUMMARY OF THE INVENTION

It has now been discovered that topical application of a formulation containing various combinations of lipids selected from the three major epidermal lipid classes or their structurally similar precursors, isomers, or analogs, will correct a defective epidermal barrier in a skin or mucous membrane disease or condition and will fortify the barrier to prevent its disruption due to environmental insults, and while certain of the lipids themselves may be generally useful as moisturizers for emolliation and hydration of the epidermis, they tend to disrupt the epidermal barrier when applied individually. The use of combinations within the scope of this invention, by contrast, do not suffer from this disadvantage, but instead produce a neutral effect on barrier function, and in certain cases improve barrier function or enhance its recovery rate.

The novel lipid formulations of this invention also enhance the therapeutic activity of other known pharmaceutical agents. Such agents include anti-inflammatory agents, antimicrobial agents, antineoplastic agents, antipruritic agents, antihistamines, analgesic agents, natural and synthetic vitamin analogs, carboxylic acids and their analogs, and artemisinin and its analogs.

By virtue of their effect on epidermal barrier function, the formulations of this invention ameliorate epidermal hyperproliferation and diminish inflammation. This results in significant prolonged or complete remission and prevents recurrences of the cutaneous lesions of papulosquamous and eczematous diseases.

DETAILED DESCRIPTION OF THE INVENTION AND PREFERRED EMBODIMENTS

The beneficial results of this invention are exhibited by the following combinations of lipids:

A. The two-component combination of cholesterol and acylceramide, combined in mole ratios ranging from 0.25:1 to 5.0:1 (cholesterol:acylceramide). Preferred ratios fall within the range of 1.5:1 to 3.5:1. A particularly preferred ratio is 2:1.

B. The three-component combination of cholesterol, acylceramide and one or more fatty acids of 12–20 carbon atom length, with 16–18 carbon atom lengths preferred. Palmitic and stearic acids are particularly preferred, with stearic acid the most preferred. Preferred mole ratio ranges for cholesterol:acylceramide:fatty acid are (0.25–5):(1–3):(1.5–3.5). More preferred are (1.5–2):1:3 with palmitic acid as the fatty acid, 4:1:2.5 with palmitic acid as the fatty acid, and 2:1:3 with stearic acid as the fatty acid.

C. The four-component combination of cholesterol, ceramide, essential fatty acid, and non-essential or bulk fatty acid of 12–20 carbon atom length. The preferred essential fatty acid is linoleic acid, and the preferred nonessential fatty acids are those of 16–18 carbon atom length, with palmitic and stearic acids the most preferred. Preferred mole ratio ranges are (2–5):(1–3):(1–3):(1.5–3.5). Preferred ratios are 3:1:1:1, 2:1:1:1, 2:2:1:1 1:1:1:2 and 1:1:1:3, particularly with the preferred fatty acids. The most preferred is 3:1:1:1, with linoleic acid as the essential fatty acid and stearic acid as the nonessential fatty acid.

D. Combinations A or B with the acylceramide replaced by a glycoceramide. The preferred glycoceramides are glucosylceramide and galactoceramide (also known as "galactocerebroside I").

E. Combinations A, B, C or D with petrolatum, glycerin or both added.

F. A glycoceramide or acylglycoceramide with trehalose as the glyco moiety.

Compounds which are termed ceramides, acylceramides or glucosylceramides are members of a class of compounds which are termed "sphingoid" compounds or "sphingolipids." These are compounds which have a backbone of sphingosine or a closely related structure, to which either fatty acids or ω-esterified fatty acids are linked through an amide linkage at the amino group of the sphingosine structure, and, in the case of glucosylceramides, those to which saccharide moieties are linked to the terminal hydroxyl of the sphingosine structure through a glycosidic bond. A generic formula for sphingoid compounds is as follows:

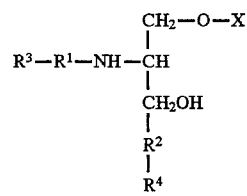

The symbols in this formula are defined as follows:

$R^1$ is either

or $CH_2$ $R^2$ is either

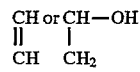

$R^3$ is any one of the following:
(i) $C_{10}$–$C_{36}$ alkyl
(ii) α-hydroxy-$C_{10}$–$C_{36}$ alkyl
(iii) ω-hydroxy-$C_{10}$–$C_{36}$ alkyl
(iv) α,ω-dihydroxy-$C_{10}$–$C_{36}$ alkyl
(v) alkanoyl as defined by the formula

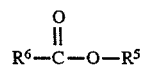

in which $R^5$ is either a divalent $C_{10}$–$C_{36}$ alkyl or a divalent α-hydroxy-$C_{10}$–$C_{36}$ alkyl, and $R^6$ is either a monovalent $C_{10}$–$C_{36}$ alkyl, preferably $C_{18}$–$C_{20}$, or a monovalent α-hydroxy-$C_{10}$–$C_{36}$ alkyl, again preferably $C_{18}$–$C_{20}$ $R^4$ is $C_{10}$–$C_{20}$ alkyl X is either H, a monosaccharide or an oligosaccharide.

The terms referred to above apply to certain subclasses of this formula, as follows:

The subclass in which $R^1$ is

$R^2$ is either

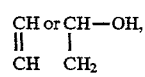

$R^3$ is alkyl or α-hydroxyalkyl, and X is H are referred to as "ceramides."

The subclass in which $R^1$ is

$R^2$ is either

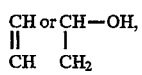

$R^3$ is alkanoyl with alkyl or α-hydroxyalkyl as both $R^5$ and $R^6$, and X is H are referred to as "ω-esterified ceramides" or "acylceramides."

The subclass in which $R^1$ is

$R^2$ is either

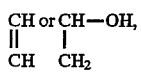

$R^3$ is alkyl or α-hydroxyalkyl, and X is a monosaccharide are referred to as "cerebrosides."

The subclass in which $R^1$ is

$R^2$ is either

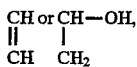

$R^3$ is alkanoyl with alkyl or α-hydroxyalkyl as both $R^5$ and $R^6$, and X is a oligosaccharide, particularly a disaccharide, are referred to as "ω-esterified cerebrosides" or "acylglycosyl sphingolipids."

The subclass in which $R^1$ is

$R^2$ is either

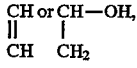

$R^3$ is alkyl or α-hydroxyalkyl, and X is a oligosaccharide, particularly a disaccharide, are also referred to as "ω-esterified cerebrosides" or as "complex glycosphingolipids."

The term "alkyl" as it is used herein includes both straight-chain and branched-chain groups, saturated and unsaturated (i.e., containing one or more double bonds), and monovalent or divalent as indicated by the position of the group in the structural formula. Straight-chain groups are generally preferred. Those groups identified as α-hydroxy alkyls are derived from α-hydroxy fatty acids, the α-position denoting the carbon adjacent to the carboxyl group in an ester or amide linkage. Certain moieties are referred to as "fatty acid residues," which term refers to the portion of a fatty acid remaining after removal of the —COOH group.

Preferred subclasses within the generic sphingoid formula are as follows:

The preferred group for $R^1$ is

The preferred group for $R^2$ is

For those compounds in which $R^3$ is other than alkanoyl, $C_{10}$–$C_{36}$ alkyl and α-hydroxy-$C_{10}$–$C_{36}$ alkyl are preferred, and the subgroup $C_{14}$–$C_{20}$ alkyl and α-hydroxy-$C_{14}$–$C_{20}$ alkyl, and alternatively, $C_{20}$–$C_{36}$ alkyl and α-hydroxy-$C_{20}$–$C_{36}$ alkyl are more preferred. Particularly preferred are saturated $C_{20}$–$C_{36}$ alkyl and saturated $C_{27}$–$C_{36}$ alkyl.

For those compounds in which $R^3$ is alkanoyl, preferred classes are those in which $R^5$ is divalent saturated $C_{20}$–$C_{36}$ alkyl or divalent saturated α-hydroxy-$C_{20}$–$C_{36}$ alkyl, particularly the former. Further preferred are those in which $R^5$ is divalent saturated $C_{27}$–$C_{36}$ alkyl. For $R^6$, preferred groups are those in which $R^6$ is monovalent $C_{10}$–$C_{24}$ alkyl, particularly monovalent unsaturated $C_{10}$–$C_{24}$ alkyl, and more particularly monovalent unsaturated $C_{14}$–$C_{20}$ alkyl. Examples of preferred $R^6$ groups are the residues of linoleic acid, linolenic acid and columbinic acid.

Preferred groups for $R^4$ are $C_{12}$–$C_{16}$ saturated straight-chain alkyl, particularly $C_{13}$–$C_{15}$ saturated straight-chain alkyl, and more particularly $C_{13}$ and $C_{15}$ saturated straight-chain alkyl.

For those compounds in which X is a saccharyl moiety, the preferred groups are glucose, galactose, fructose, lactose and trehalose. Of these, glucose and galactose are preferred in certain cases, while trehalose is preferred in others.

Many of these compounds are naturally occurring, particularly in the mammalian stratum corneum and other mammalian tissue. Ceramides and cerebrosides can be extracted from brain tissue, nervous tissue and other mammalian tissue, notably bovine brain, and human spleen tissue. The term "galactocerebroside type I," for example, represents a mixture which is extracted from bovine brain, and the $R^3$ moiety is approximately 98% α-hydroxy acids. A mixture termed "galactocerebroside type II" is likewise extracted from bovine brain, and differs from "galactocerebroside type I" by being approximately 98% non-hydroxy fatty acids, primarily nervonic and lignoceric acids, for the $R^3$ moiety. Nervonic and lignoceric acids are both 24-carbon fatty acids, nervonic being unsaturated by virtue of one double bond, and lignoceric being saturated. A mixture termed "ceramides type III" is prepared by the action of phospholipase C on bovine brain sphingomyelin, and the $R^3$ moiety is primarily stearic (18-carbon saturated) and nervonic acids. A mixture termed "ceramides type IV" is similar to ceramides type III except that it contains α-hydroxy acids rather than stearic and nervonic acids. All of these mixtures are commercially available from major chemical suppliers such as Sigma Chemical Company, St. Louis, Mi., U.S.A., and those which are not direct extracts from mammalian tissue are capable of being prepared by techniques described in the literature, such as Morrison, W. R., *Biochem. Biophys. Acta* 176:537 (1969), and Carter, H. E., et al., *J. Lipid Res.* 2:228 (1961).

Certain specific sphingoid compounds are particularly preferred. Among the ceramides and cerebrosides, the preferred compounds are bovine ceramides, types III and IV, and bovine cerebrosides, types I and II. Among the ω-esterified ceramides and cerebrosides, the preferred compounds are N-(ω-O-linoleyl)-triacontanoyl-eicosasphingenine, N-(ω-O-linoleyl)-dotriacontanoyl-eicosasphingenine, glucosyl-β1-N-(ω-O-linoleyl)-triacontanoyl-eicosasphingenine, glucosyl-β1-N-(ω-O-linoleyl)-dotriacontanoyl-eicosasphingenine, and glucosyl-β1-N-(ω-O-linoleyl)-triacontanoyl-trihydroxyeicosasphingenine.

The cerebrosides can be prepared from the ceramides, and ω-esterified cerebrosides from ω-esterified ceramides, by glycosylation. Likewise, ceramides can be prepared from cerebrosides, and ω-esterified ceramides from ω-esterified cerebrosides, by deglycosylation. ω-Esterified ceramides can be prepared from ω-hydroxyceramides by esterification with the appropriate carboxylic acids. Techniques for each of these types of reaction are known in the art.

For the components which are characterized as fatty acids, the term "fatty acid" includes both α-hydroxy fatty acids and non-hydroxylated fatty acids, as well as saturated and unsaturated fatty acids, and straight-chain and branched-chain fatty acids. Straight-chain, non-hydroxylated fatty acids are preferred. The fatty acids are generally up to 25 carbon atoms in length. Examples are palmitic (16-carbon, saturated), stearic (18-carbon, saturated), linoleic (18-carbon, two double bonds), linolenic (18-carbon, three double bonds), columbinic (18-carbon, three double bonds, a trans-isomer of linolenic), arachidic (20-carbon, saturated), arachidonic (20 carbon, four double bonds), lignoceric (24-carbon, saturated), and nervonic (24-carbon, one double bond) acids. Acids of 12 to 20 carbon atoms are preferred.

Preferred essential fatty acids are columbinic and linoleic acids, with linoleic acid being the most preferred. Non-essential or bulk fatty acids are all other fatty acids. Among these, palmitic and stearic acids are preferred, with palmitic acid the most preferred. Esters of fatty acids are lower alkyl esters, the alkyl moiety being general 6 carbon atoms or less. Preferred esters are glycerides, such as triglycerides. Vegetable oils may be used as the fatty acids and fatty acid esters. Examples are corn oil (linoleic, oleic, palmitic and stearic acids), safflower oil (primarily linoleic acid), sunflower oil (primarily mixed triglycerides of linoleic and oleic acids), soybean oil (primarily linoleic and linolenic acids), and peanut oil (primarily linoleic and linolenic acids).

The beneficial effect of the lipid combinations of this invention are that they allow or stimulate the stratum corneum barrier function to be normal or accelerated four hours after an acute injury, indicating that barrier recovery was normalized or enhanced even if it had been delayed early, i.e., initially perturbed or aggravated by the application of the lipids. Preferred lipid combinations in accordance with this invention are those which significantly accelerate stratum corneum barrier recovery four hours after acute injury. Among all compositions of this invention, these compositions are the most effective therapeutic agents for skin disorders.

The total lipid contents in topical formulations in accordance with this invention are not critical and vary over a wide range, even to the upper limit of dissolvability. In general, the total lipid content ranges from 0.1% to 60% by weight. A preferred range is 1% to 20% by weight.

Topical formulations containing the lipid combinations of the present invention are applied to beneficial effect to skin and/or mucus membranes. The formulations will include the lipids dispersed or dissolved in a pharmaceutically acceptable carrier, which includes any of the wide variety of vehicles used for application of a medicament to the epidermis. These vehicles are well known in the art. The formulations may assume any of various forms. Examples are lotions, solutions, gels, creams, emollient creams, unguents and sprays. For many applications, it will be of benefit to include a variety of inactive agents in the formulations to promote even spreading of the formulation over the affected area. Examples of these inactive agents are surfactants, humectants, wetting agents, emulsifiers, or propellants.

The term "therapeutically effective amount" refers to any amount that will cause a substantial relief of symptoms when applied repeatedly over time. The optimum amounts in any given instance will be readily apparent to those skilled in the art or are capable of determination by routine experimentation.

The formulations of this invention may also function as a base for the delivery of other therapeutic agents, and when so used, will enhance the clinical response to such agents. Examples of these other therapeutic agents are:

1) Anti-inflammatory agents, examples of which are corticosteroids, colchicine, sulfasalazine, and sulfones;
2) Antibiotics, examples of which are quinolones, macrolides, penicillins, cephalosporins, sulfonamides, and tetracyclines;
3) Antivirals, examples of which are acyclovir, idoxuridine, zidovudine, ddI, vidarabine, and trifluridine;
4) Antifungals, examples of which are ketoconazole, econazole, griseofulvin, cicloprix, and naftidine;
5) Antihistamines, examples of which are diphenhydramine, astemizole, hydroxyzine, doxepin, amitriptyline, cyproheptadine, and sodium cromolyn;
6) Antipruritics, examples of which are camphor, menthol, phenol, benzocaine, benzyl alcohol, salicylic acid, dyclonine, and pramoxine;
7) Antineoplastic agents, examples of which are methotrexate, piritrexim, cisplatin, 5-fluorouracil, bleomycin, carmustine, hydroxyurea, azathioprine, and nitrogen mustard;
8) Carboxylic acid analogs, examples of which are 1-monolaurin, azelaic acid and dodecanedioic acid;
9) Natural and synthetic vitamins and analogs, examples of which are vitamin D, calcipitriol, 1,25-dihydroxy cholecalciferol, retinol, retinyl palmitate, retinyl ascorbate, isotretinoin, etretinate and retinoic acid; and
10) Artemisinin analogs, examples of which are artesunate, arteether, artemether, dihydroartemisinin and artelenic acid;

The concentrations of these non-lipid therapeutic ingredients may vary widely. A typical range is from about 0.01% to about 10%. The most appropriate concentration will depend on the clinical indication and will be apparent to those skilled in the art.

Formulations employing the lipid combinations of this invention will successfully treat and prevent diseases and disorders of the skin and mucous membranes which cause disruption or dysfunction of the epidermal barrier. As a result, these formulations may be effectively applied to any of the following conditions:

1) Premature infants under 33 weeks gestational age
2) Atopic and seborrheic dermatitis and other genetically predisposed dermatitides
3) Eczematous dermatitis induced by environmental or occupational insults, specifically allergic and irritant contact, eczema craquelée, photoallergic, phototoxic, phytophotodermatitis, radiation and stasis dermatitis
4) Ulcers and erosions due to cutaneous trauma including chemical or thermal burns or vascular compromise or ischemia including venous, arterial, embolic or diabetic ulcers
5) Ichthyoses
6) Epidermolysis bullosa
7) Psoriasis and other papulosquamous diseases
8) Cutaneous changes of intrinsic aging and/or dermatoheliosus
9) Mechanical friction blistering
10) Corticosteroid atrophy, for reversal and prevention
11) As a base for use with other known or potential therapeutic agents which produce cutaneous irritancy and/or disrupt the epidermal barrier
12) A need to fortify the epidermal barrier to prevent occupationally or environmentally induced or genetically predisposed cutaneous disorders The optimum methods and frequency of administration of these formulations will be readily apparent to those skilled in the art or are capable of determination by routine experimentation. Effective results in most cases are achieved by topical application of a thin layer over the affected area, or the area where one seeks to achieve the desired effect. Depending on the condition being addressed, its stage or degree, and whether application is done for therapeutic or preventive reasons, effective results are achieved with application rates of from one application every two or three days to four or more applications per day.

The invention is generally applicable to the treatment of mammalian skin, including for example humans, domestic pets, and livestock and other farm animals.

The following examples are offered for purposes of illustration. They are intended neither to define nor limit this invention in any manner.

The abbreviations used in the following examples and tables are as follows:

AC: N-($\omega$-O-linoleyl)-dotriacontanoyl-eicosasphingenine, a sphingosine-based acyl ceramide with a 30-carbon atom acid moiety at the amide linkage, $\omega$-esterified with linoleic acid Cer: bovine ceramide CH: cholesterol LA: linoleic acid PA: palmitic acid SA: stearic acid GC: galactocerebroside I, a glycosphingolipid with galactose as the glycosyl moiety T: glycosphingolipid with trehalose as the glycosyl moiety pet: petrolatum gly: glycerin

EXAMPLE 1

This example reports measurements of skin conductance following treatment with formulations in accordance with the invention, as well as formulations outside the scope of the invention. Skin conductance is a measure of the water content of the stratum corneum, and the higher the mean conductance, the higher the water content of the skin and the more potent the moisturizer.

The test formulations were prepared by combining the lipids in selected mole ratios with a vehicle consisting of a mixture of propylene glycol and ethanol at a volume:volume ratio of 7:3. The concentration of the lipids in the formulations was 1.2% by weight. Two commercially available products were included in the test for comparison. These were LacHydrin® V and Avon ANEW®.

The test procedure was as follows. Twelve female humans aged 18–55, in two panels of six each, were pretreated for one week by washing their forearms daily with Ivory Soap. Following the pretreatment, the test formulations were applied to three sites on the volar side of each forearm. Skin conductance was measured prior to application of the formulations to establish a baseline, and again at four hours after application of the formulations. Measurements were taken using a SKICON® 200 MT probe. The mean values are shown in Table A below. The results show that all of these formulations serve as effective moisturizing agents, with the greatest benefit observed from the formulation which includes petrolatum and glycerine.

TABLE A

MEAN CONDUCTANCE -
As Measure of Moisturizing Capability

| Composition Applied (mole ratios) | Mean Conductance (siemens) |
|---|---|
| Panel 1: | |
| None (measurement taken prior to treatment with test formulation) | −1.9 |
| LacHydrin ® V | 237.7 |
| Avon ANEW ® | 624.4 |
| Vehicle plus additives shown below (vehicle is propylene glycol/ethanol, 7:3, additives totaling 2–3% by weight of formulation): | |
| CH/AC/SA (2:1:1) | 69.6 |
| CH/GC/LA/PA (1:1:1:3) | 89.9 |
| CH/GC/AC/SA (2:1:1:3) | 95.4 |
| CH/AC (3:1) | 111.4 |
| Panel 2: | |
| None (measurement taken prior to treatment with test formulation) | 4.7 |
| Arden Ceramide Droplets | 57.7 |
| Vehicle plus additives shown below (vehicle is propylene glycol/ethanol, 7:3, additives totaling 2–3% by weight of formulation): | |
| CH/AC (2:1) | 126.9 |
| CH/Cer/LA/PA (3:1:1:1) | 122.4 |
| CH/AC/PA (4:1:2.5) | 130.4 |
| 50% CH/AC (2:1), 25% pet, 25% gly | 383.2 |

EXAMPLE 2

The ability of formulations of the present invention to repair a disrupted barrier function of the epidermis was tested as follows.

Hairless mice, aged 8 to 12 weeks, were treated by repeated applications of absolute acetone to one flank to perturb the cutaneous barrier. The rate of trans-epidermal water loss (TEWL) was then measured periodically by use of an electrolytic water analyzer (Meeco, Inc., Warrington, Pa.). As soon as the TEWL rates exceeded 2.0 g/m²/h, test formulations were applied topically to the barrier-perturbed areas, each formulation applied over an area of 5 cm², the formulations consisting of either a lipid or lipid combination dissolved in a vehicle consisting of a mixture of propylene glycol and ethanol at a volume/volume ratio of 7:3, or the vehicle alone. Each test formulation was applied to 10–12 mice. Further measurements of TEWL were then taken at 45 minutes, 4 hours and 8 hours after application of the test formulations. The values from these measurements were compared with the values obtained just before the test formulations were applied to determine the degree of barrier recovery. The results are shown in Table B below, where the TEWL is shown as a percent of the value prior to application of the test formulations. The degrees of recovery for each lipid or lipid combination can be compared with the values obtained with the vehicle alone to determine what effect can be attributed to the inclusion of the lipid or lipid combination.

In the table, the values listed in the second, third and fifth columns represent the TEWL at 45 minutes, 4 hours and 8 hours, respectively, after application of each test formulation. The values are expressed as percentages of the TEWL immediately before the test formulations were applied. Percentages below 100, therefore, indicate recovery of barrier function, although recovery attributable to the lipid(s) is seen only when the percentages fall below those obtained for the vehicle alone. Percentages above 100 indicate further deterioration of barrier function rather than recovery, the further deterioration attributable to the test formulation. Although not shown in the table, use of the formulations within the scope of this invention resulted in 0% TEWL, or full recovery of the stratum corneum, at 30–36 hours after application.

Table B shows that while many formulations serve effectively as moisturizing agents, only a select few also serve as effective agents for repair of barrier function. For example, the table indicates that petrolatum alone lowers the TEWL to 50.1% at four hours, while combining the petrolatum with a 3:1:1:1 combination of cholesterol, ceramide, linoleic acid and palmitic acid lowers the percent TEWL further to 41.6%. As a further example, NEUTROGENA® Norwegian Hand Cream lowers the TEWL to 37.0%, but combining this cream with a 1:1 combination of cholesterol and acylceramide lowers the TEWL further to 18.3%. Other beneficially performing combinations are evident from the table.

TABLE B

BARRIER FUNCTION RECOVERY
Trans-Epidermal Water Loss at Various Intervals Expressed as
Percent of Trans-Epidermal Water Loss at 0 Hours (Maximum Level)

| Composition Applied (mole ratios of active ingredients) | TEWL at 0.75 Hours (as % of TEWL at 0 Hours) | TEWL at 4 Hours (as % of TEWL at 0 Hours) | P Value (ND: no deviation; NS: not significant) | TEWL at 8 Hours (as % of TEWL at 0 Hours) |
|---|---|---|---|---|
| Test Series 1: | | | | |
| Vehicle alone (propylene glycol/ethanol, 7:3) Vehicle plus (additive at 2–3% by weight): | 87.0 | 67.5 | ND | 44.6 |
| Cer | — | 113.8 | 0.001 | — |
| AC | — | 93.5 | 0.01 | — |
| CH | — | 69.5 | NS | — |
| PA | — | 67.3 | NS | — |
| SA | — | 69.1 | NS | — |
| pet | 49.2 | 50.1 | 0.01 | — |
| gly | 88.3 | 53.1 | 0.1 | 29.1 |
| T | — | 58.0 | 0.1 | — |
| CH/Cer (1:1) | — | 91.7 | 0.01 | — |
| CH/LA (1:1) | — | 88.0 | 0.01 | — |
| CH/Cer/LA (1:1:1) | — | 66.0 | NS | — |
| CH/Cer/PA (1:1:1) | — | 66.8 | NS | — |
| CH/Cer/SA (1:1:1) | — | 67.4 | NS | — |
| Test Series 2: | | | | |
| Vehicle alone (propylene glycol/ethanol, 7:3) Vehicle plus (additive totaling 2–3% by weight): | — | 66.6 | ND | — |
| CH/AC (0.25:1) | — | 50.2 | 0.01 | — |
| CH/AC (0.67:1) | — | 23.6 | 0.0005 | — |
| CH/AC (1.33:1) | — | 26.9 | 0.001 | — |
| CH/AC (1.5:1) | — | 18.4 | 0.0001 | — |
| CH/AC (2:1) | 102.3 | 17.4 | 0.0001 | 11.0 |
| CH/AC (2.5:1) | — | 24.5 | 0.0005 | — |
| CH/AC (3:1) | — | 22.1 | 0.0001 | — |
| CH/AC (3.5:1) | — | 20.3 | 0.0001 | — |
| CH/AC (4.6:1) | — | 47.0 | 0.01 | — |
| 75% CH/AC (2:1) 25% pet | 43.1 | 21.0 | 0.0001 | 10.1 |
| 75% CH/AC (2:1) 25% gly | 82.4 | 16.8 | 0.0001 | 8.0 |

TABLE B-continued

BARRIER FUNCTION RECOVERY
Trans-Epidermal Water Loss at Various Intervals Expressed as
Percent of Trans-Epidermal Water Loss at 0 Hours (Maximum Level)

| Composition Applied (mole ratios of active ingredients) | TEWL at 0.75 Hours (as % of TEWL at 0 Hours) | TEWL at 4 Hours (as % of TEWL at 0 Hours) | P Value (ND: no deviation; NS: not significant) | TEWL at 8 Hours (as % of TEWL at 0 Hours) |
|---|---|---|---|---|
| 50% CH/AC (2:1) 25% pet 25% gly | 40.2 | 17.9 | 0.0001 | 7.0 |
| 75% CH/AC (4:1) 25% pet | 47.6 | 33.9 | 0.001 | 22.3 |
| 75% CH/AC (4:1) 25% gly | 109.6 | 37.3 | 0.001 | 17.5 |
| CH/AC/PA (3:1:1) | — | 26.9 | 0.001 | — |
| CH/AC/PA (4:1:2.5) | — | 26.8 | 0.001 | — |
| CH/AC/SA (2:1:2) | — | 28.7 | 0.001 | — |
| CH/AC/SA (2:1:3) | 94.7 | 17.6 | 0.0001 | 5.8 |
| CH/AC/SA (2:1:4) | — | 28.1 | 0.001 | — |
| 50% CH/AC/SA (2:1:3) 25% pet 25% gly | 30.6 | 13.9 | 0.00005 | 6.7 |
| CH/GC/LA/SA (1:1:1:1) | — | 77.3 | NS | — |
| Test Series 3: | | | | |
| Vehicle alone (propylene glycol/ethanol, 7:3) | — | 67.5 | ND | — |
| Vehicle plus (additives totaling 2-3% by weight): | | | | |
| CH/Cer/LA/PA (1:1:1:1) | — | 60.7 | NS | — |
| CH/Cer/LA/PA (2:1:1:1) | — | 37.4 | 0.001 | — |
| 75% CH/Cer/LA/PA (3:1:1:1) 25% pet | — | 41.6 | 0.05 (vs. pet) | — |
| CH/Cer/LA/PA (3:1:1:1) | — | 28.0 | 0.001 | — |
| CH/Cer/LA/PA (4:1:1:1) | — | 49.5 | 0.01 | — |
| CH/Cer/LA/PA (5:1:1:1) | — | 56.5 | 0.1 | — |
| CH/Cer/LA/PA (5.5:1:1:1) | — | 61.5 | NS | — |
| CH/Cer/LA/PA (1:1:1:1.5) | — | 58.6 | 0.1 | — |
| CH/Cer/LA/PA (1:1:1:2) | — | 46.0 | 0.01 | — |
| CH/Cer/LA/PA (1:1:1:3) | — | 32.0 | 0.001 | — |
| CH/Cer/LA/PA (1:1:1:3.5) | — | 56.0 | 0.1 | — |
| CH/Cer/LA/PA (1:1:1:4) | — | 69.7 | NS | — |
| CH/Cer/LA/SA (1:1:1:2) | — | 50.2 | 0.01 | — |
| CH/Cer/LA/SA (1:1:1:3) | — | 34.8 | 0.001 | — |
| 75% CH/Cer/LA/PA (3:1:1:1) 25% pet | 51.7 | 41.6 | 0.01 | — |
| CH/Cer/LA/PA (2:2:1:1) | — | 36.6 | 0.001 | — |
| Test Series 4: | | | | |
| Vehicle alone (propylene glycol/ethanol, 7:3) | — | 66.6 | ND | — |
| Avon ANEW ® | — | 71.9 | NS | — |
| LacHydrin ® V | — | 63.8 | NS | — |
| Arden Ceramide Droplets | — | 52.9 | 0.1 | — |
| LACTICARE ® | — | 50.2 | 0.01 | — |
| Vehicle plus (additives totaling 2-3% by weight): | | | | |

TABLE B-continued

BARRIER FUNCTION RECOVERY
Trans-Epidermal Water Loss at Various Intervals Expressed as
Percent of Trans-Epidermal Water Loss at 0 Hours (Maximum Level)

| Composition Applied (mole ratios of active ingredients) | TEWL at 0.75 Hours (as % of TEWL at 0 Hours) | TEWL at 4 Hours (as % of TEWL at 0 Hours) | P Value (ND: no deviation; NS: not significant) | TEWL at 8 Hours (as % of TEWL at 0 Hours) |
|---|---|---|---|---|
| CH/Cer/AC/LA/PA (3:1:0.5:1:1) | — | 30.7 | 0.001 | — |
| CH/Cer/AC/LA/PA (4:1:0.5:1:2) | — | 32.9 | 0.001 | — |
| CH/Cer/AC/LA/PA (4.5:0.5:1:0.5:1.5) | — | 32.8 | 0.001 | — |
| CH/Cer/AC/LA/PA (4:1:0.5:2:1) | — | 46.7 | 0.01 | — |
| Test Series 5: | | | | |
| Vehicle alone (NEUTROGENA® Hand Cream) | — | 37.0 | ND | 20.9 |
| Vehicle plus (additives totaling 2–3% by weight): | | | | |
| CH/AC (1:1) | — | 18.6 | 0.0001 | 9.2 |
| CH/AC (2:1) | — | 24.6 | 0.001 | 7.0 |
| CH/AC/PA (4:1:2.5) | — | 23.5 | 0.001 | 8.5 |
| CH/AC/PA (3:1:1) | — | 28.9 | 0.02 | 21.2 |
| CH/AC/PA/Cer/La (4:0.5:2:1:1) | — | 26.0 | 0.001 | 14.3 |
| Test Series 6: | | | | |
| Vehicle alone (NEUTROGENA® Hand Cream) | — | 30.2 | ND | — |
| Vehicle plus (additives totaling 2–3% by weight): | | | | |
| CH/Cer/PA (2:1:1) | — | 23.2 | 0.05 | — |
| CH/Cer/LA/PA (2:2:1:1) | — | 22.0 | 0.05 | — |
| CH/Cer/LA/SA (1:1:1:3) | — | 19.2 | 0.001 | — |
| Test Series 7: | | | | |
| Vehicle alone (NEUTROGENA® Hand Cream) | —' | 20.8 | ND | 23.4 |
| Vehicle plus (additives totaling 2–3% by weight): | | | | |
| CH/GC/LA/PA (1:1:1:3) | — | 11.2 | 0.01 | 9.8 |
| CH/GC/LA/PA (1:3:1:1) | — | 23.9 | NS | 13.7 |

TABLE C

STATISTICAL SIGNIFICANCE -
Condensation of Data from Table B

| Composition | TEWL at 4 Hours (as % of TEWL at 0 Hours) | P Value Relative to Vehicle |
|---|---|---|
| CH/AC (1.5:1) | 18.4 | <0.01 |
| CH/AC (2.5:1) | 24.5 | <0.01 |
| CH/AC (3.5:1) | 20.3 | <0.01 |
| CH/AC (2:1.5) | 26.9 | <0.001 |
| CH/AC (2:3) | 23.6 | <0.01 |
| CH/AC (2:1) | 17.4 | <0.2 |
| 75% CH/AC (2:1), 25% pet | 21.0 | <0.01 |
| 75% CH/AC (2:1), 25% gly | 16.8 | NS |
| 50% CH/AC (2:1), 25% pet, 25% gly | 17.9 | <0.2 |
| CH/AC/SA (2:1:3) | 17.6 | <0.2 |
| 50% CH/AC/SA (2:1:3), 25% pet, 25% gly | 13.9 | ND |

TABLE C-continued

STATISTICAL SIGNIFICANCE -
Condensation of Data from Table B

| Composition | TEWL at 4 Hours (as % of TEWL at 0 Hours) | P Value Relative to Vehicle |
|---|---|---|
| CH/AC/SA (2:1:2) | 28.7 | <0.0001 |
| CH/AC/SA (2:1:4) | 28.1 | <0.0001 |
| CH/GC/LA/SA (2:1:1:3) | 23.8 | <0.001 |
| CH/GC/LA/SA (1:1:1:1) | 77.3 | <0.0001 |
| CH/GC/LA/SA (2:1:1:2) | 39.6 | <0.0001 |
| CH/GC/AC/SA (2:1:1:3) | 29.5 | <0.0001 |
| 50% CH/GC/AC/SA (2:1:1:3), 25% pet, 25% gly | 17.7 | <0.2 |
| Elizabeth Arden Ceramide Droplets | 52.9 | <0.0001 |
| LACHYDRIN ® 5% Lotion | 63.8 | <0.0001 |
| Avon ANEW ® Lotion | 71.9 | <0.0001 |
| LACTICARE ® Lotion | 50.2 | <0.0001 |
| petrolatum | 50.1 | <0.0001 |
| NEUTROGENA ® Hand Cream | 37.0 | <0.0001 |
| glycerin | 53.1 | <0.1 |

TABLE D

COMPARATIVE STATISTICAL SIGNIFICANCE

| Composition | TEWL at 4 Hours (as % of TEWL at 0 Hours) | P Value Relative to Best Value |
|---|---|---|
| 50% CH/AC/SA (2:1:3), 25% pet, 25% gly | 13.9 | ND |
| CH/AC (2:1) | 17.4 | <0.2 |
| CH/Cer/LA/PA (3:1:1:1) | 28.0 | <0.0001 |
| CH/AC/PA (3:1:1) | 26.9 | <0.0001 |
| CH/AC/PA (4:1:2.5) | 26.8 | <0.001 |
| 75% CH/AC (2:1), 25% gly | 16.8 | ND |
| 75% CH/AC (2:1), 25% pet | 21.0 | <0.2 |
| 50% CH/AC (2:1), 25% pet, 25% gly | 17.9 | NS |
| CH/AC (2:1) | 17.4 | NS |
| 50% CH/GL/AC/SA (2:1:1:3), 25% gly, 25% pet | 17.7 | ND |
| CH/GC/AC/SA (2:1:1:3) | 29.5 | <0.001 |
| CH/GC/LA/SA (2:1:1:3) | 23.8 | <0.02 |

The remaining examples in this specification illustrate the moisturization capabilities of formulations within the scope of this invention.

EXAMPLE 3

Topical Formulation A was prepared by first heating the lipid phase components listed below at 70° C. to convert them to liquid form, then combining the liquified lipid phase with the aqueous phase components listed below, similarly heated, and mixing the two phases with the sodium lauryl sulfate emulsifier. This produced an emulsion in the form of a lotion.

The mole ratio of cholesterol to acylceramide in the lipid phase was 4:1.

| | Weight Percent |
|---|---|
| Lipid Phase | |
| Cholesterol | 7.72 |
| Acylceramide* | 4.28 |
| Aqueous Phase | |
| Sodium Lauryl Sulfate 30% solution | 7.00 |
| Glycerol | 2.00 |
| Imidazolidynyl Urea | 0.30 |
| Methyl Paraben | 0.20 |
| Propyl Paraben | 0.05 |
| Distilled water | balance |

*The term "acylceramide" as it is used in this example is one which has the general formula shown above for the ceramide-based compound with

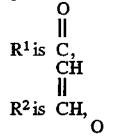

$R^1$ is $C$,
     $\overset{\overset{CH}{\|}}{}$
$R^2$ is $CH$,
$R^3$ is $R^6-\overset{O}{\overset{\|}{C}}-O-R^5$ in which $R^5$ is a divalent saturated 29-carbon-length alkyl chain,
$R^6$ is a linoleate residue, and X is H.

EXAMPLE 4

Topical Formulation B was prepared in the same manner as Formulation A, again producing a creamy emulsion. The mole ratio of cholesterol to galactocerebroside I to linoleic acid in the lipid phase was 3:1:1.

| | Weight Percent |
|---|---|
| Lipid Phase | |
| Cholesterol | 17.37 |
| Galactocerebroside I | 11.09 |
| Linoleic Acid | 4.20 |
| Aqueous Phase | |
| Sodium Lauryl Sulfate 30% solution | 7.00 |
| Glycerol | 3.00 |
| Imidazolidynyl Urea | 0.30 |
| Methyl Paraben | 0.20 |
| Propyl Paraben | 0.05 |
| Distilled water | balance |

EXAMPLE 5

Five health care workers whose daily routine involved frequent changes of gloves and hand washing and who all suffered from noninflammatory, scaly, intermittently pruritic hands as a result experienced only minimal relief by standard moisturizing lotions and partially relief by occlusive greases such as Aquaphor. Application of Formula A three times by each worker daily completely relieved the scaling and symptoms within an average of 6 days. Continued use of the product every other day effectively maintained normal skin despite the workers' continued exposure to the same environmental insults.

EXAMPLE 6

Three people with atopic dermatitis in remission all suffered from marked xerosis, but not ichthyosis which is most prominent on the distal extremities. All three people tried commercially sold moisturizing agents, and in all three cases, the condition showed no improvement. The use of occlusive hydrocarbon mixtures such as Vaseline produced pruritus.

Formulation B applied two to four times daily produced complete resolution of xerosis within three to four days. Daily application for maintenance prevented recurrence.

EXAMPLE 7

Topical Formulation C was prepared by heating the lipids listed below to 70° C. to convert them to liquid form, followed by mixing the liquified lipids together with the aqueous phase components listed below and the sodium lauryl sulfate emulsifer. The mole ratio of (cholesterol):(ceramide):(linoleic acid):(palmitic acid) in the lipid phase was 3:1:1:1. The result was a creamy emulsion.

|  | Weight Percent |
| --- | --- |
| Lipid Phase |  |
| Cholesterol | 11.61 |
| Bovine Ceramide, Type III | 5.37 |
| Linoleic Acid | 2.80 |
| Palmitic Acid | 2.57 |
| Aqueous Phase |  |
| Sodium Lauryl Sulfate 30% solution | 7.00 |
| Glycerol | 2.50 |
| Imidazolidynyl Urea | 0.30 |
| Methyl Paraben | 0.20 |
| Propyl Paraben | 0.05 |
| Distilled water | balance |

EXAMPLE 8

Four middle-aged women, all outdoor agriculture workers and all of whom had scaly, leathery-textured, finely wrinkled facial skin, experienced only poor response to a variety of moisturizing lotions. Each of the women applied Topical Formulation C twice daily, and the scaling was cleared within one week in all cases. After four weeks of twice daily application, the skin of all four women exhibited a noticeable improvement in suppleness and skin turgor.

The foregoing is offered primarily for purposes of illustration. It will be readily apparent to those skilled in the art that the components, additional ingredients, proportions, methods of administration, and other parameters of the invention described herein may be further modified or substituted in various ways while still remaining within the invention.

What is claimed is:

1. A method for treating the epidermis of a terrestrial mammal suffering from a condition characterized by a perturbed epidermal barrier function, said method comprising topically applying to said epidermis a therapeutically effective amount of a pharmaceutical composition comprising the lipids:
    (a) cholesterol, and
    (b) an acylceramide,
the mole ratio of lipid (a) to lipid (b) being from about 0.25:1 to about 5:1.

2. A method in accordance with claim 1 in which said mole ratio is from about 1.5:1 to about 3.5:1, and the acyl group of said acylceramide is an acyl group of a fatty acid containing 18 to 20 carbon atoms.

3. A method in accordance with claim 1 in which said mole ratio is about 2:1, and the acyl group of said acylceramide is an acyl group of a fatty acid containing 18 to 20 carbon atoms.

4. A method for treating the epidermis of a terrestrial mammal suffering from a condition characterized by a perturbed epidermal barrier function, said method comprising topically applying to said epidermis a therapeutically effective amount of a pharmaceutical composition comprising the lipids:
    (a) cholesterol,
    (b) an acylceramide,
    (c) at least one fatty acid of 12 to 20 carbon atoms in length, the mole ratios of lipids (a):(b):(c) being within the ranges (0.25–5):(1–3):(1.5–3.5).

5. A method in accordance with claim 4 in which the acyl group of said acylceramide is an acyl group of a fatty acid containing 18 to 20 carbon atoms, and lipid (c) is a fatty acid of 16–18 carbon atoms.

6. A method in accordance with claim 4 in which the acyl group of said acylceramide is an acyl group of a fatty acid containing 18 to 20 carbon atoms; lipid (c) is palmitic acid; and the mole ratios of lipids (a):(b):(c) are (1.5–2):1:3.

7. A method in accordance with claim 4 in which the acyl group of said acylceramide is an acyl group of a fatty acid containing 18 to 20 carbon atoms; lipid (c) is palmitic acid; and the mole ratios of lipids (a):(b):(c) are 4:1:2.5.

8. A method in accordance with claim 4 in which the acyl group of said acylceramide is an acyl group of a fatty acid containing 18 to 20 carbon atoms; lipid (c) is stearic acid; and the mole ratios of lipids (a):(b):(c) are 2:1:3.

9. A method for treating the epidermis of a terrestrial mammal suffering from a condition characterized by a perturbed epidermal barrier function, said method comprising topically applying to said epidermis a therapeutically effective amount of a pharmaceutical composition comprising the lipids:
    (a) cholesterol,
    (b) a ceramide,
    (c) an essential fatty acid, and
    (d) a nonessential fatty acid of 12 to 20 carbon atoms in length, the mole ratios of lipids (a):(b):(c):(d) being within the ranges (2–5):(1–3):(1–3):(1.5–3.5).

10. A method in accordance with claim 9 in which said essential fatty acid is linoleic acid, and said nonessential fatty acid is a member selected from the group consisting of palmitic and stearic acids.

11. A method in accordance with claim 9 in which said essential fatty acid is linoleic acid, and said nonessential fatty acid is a member selected from the group consisting of palmitic and stearic acids, and the mole ratios of lipids (a):(b):(c):(d) are selected from the group consisting of 3:1:1:1, 2:1:1:1, 2:2:1:1, 1:1:1:2, and 1:1:1:3.

12. A method in accordance with claim 9 in which said essential fatty acid is linoleic acid, and said nonessential fatty acid is stearic acid, and the mole ratios of lipids (a):(b):(c):(d) are 3:1:1:1.

13. A method for treating the epidermis of a terrestrial mammal suffering from a condition characterized by a perturbed epidermal barrier function, said method comprising topically applying to said epidermis a therapeutically effective amount of a pharmaceutical composition comprising the lipids:
    (a) cholesterol, and
    (b) a glycoceramide, the mole ratio of lipid (a) to lipid (b) being from about 0.25:1 to about 5:1.

14. A method in accordance with claim 13 in which lipid (b) is a member selected from the group consisting of glucosylceramide and galactoceramide.

15. A method for treating the epidermis of a terrestrial mammal suffering from a condition characterized by a perturbed epidermal barrier function, said method comprising topically applying to said epidermis a therapeutically effective amount of a pharmaceutical composition comprising the lipids:

(a) cholesterol, (b) a glycoceramide, (c) at least one fatty acid of 12 to 20 carbon atoms in length, the mole ratios of lipids (a):(b):(c) being within the ranges (0.25–5):(1–3):(1.5–3.5).

16. A method in accordance with claim 15 in which lipid (b) is a member selected from the group consisting of glucosylceramide and galactoceramide.

17. A method for treating the epidermis of a terrestrial mammal suffering from a condition characterized by a perturbed epidermal barrier function, said method comprising topically applying to said epidermis a therapeutically effective amount of a member selected from the group consisting of glycoceramides and acylglycoceramides in which the glyco moiety is trehalose.

18. A method in accordance with claims 1, 4, 9, 13, 15 or 17 in which said pharmaceutical composition further comprises a member selected from the group consisting of petrolatum, glycerin, and a mixture of petrolatum and glycerin.

19. A method in accordance with claims 1, 4, 9, 13, 15 or 17 in which said lipids together comprise from about 0.1% to about 60% by weight of said pharmaceutical composition, the remainder being a pharmaceutically acceptable carrier.

20. A method in accordance with claims 1, 4, 9, 13, 15 or 17 in which said lipids together comprise from about 1% to about 20% by weight of said pharmaceutical composition, the remainder being a pharmaceutically acceptable carrier.

* * * * *